(12) United States Patent
Oki et al.

(10) Patent No.: US 11,353,434 B2
(45) Date of Patent: Jun. 7, 2022

(54) MOLECULAR DETECTION APPARATUS AND MOLECULAR DETECTION METHOD

(71) Applicant: KABUSHIKI KAISHA TOSHIBA, Minato-ku (JP)

(72) Inventors: Mitsuhiro Oki, Kawasaki (JP); Hirohisa Miyamoto, Kamakura (JP); Ko Yamada, Yokohama (JP)

(73) Assignee: KABUSHIKI KAISHA TOSHIBA, Minato-ku (JP)

( * ) Notice: Subject to any disclaimer, the term of this patent is extended or adjusted under 35 U.S.C. 154(b) by 493 days.

(21) Appl. No.: 15/706,216

(22) Filed: Sep. 15, 2017

(65) Prior Publication Data

US 2018/0275105 A1    Sep. 27, 2018

(30) Foreign Application Priority Data

Mar. 21, 2017    (JP) .............................. JP2017-054569

(51) Int. Cl.
*G01N 33/00*    (2006.01)
*G01N 33/497*    (2006.01)
(Continued)

(52) U.S. Cl.
CPC ............. *G01N 30/54* (2013.01); *G01N 30/70* (2013.01); *G01N 33/0018* (2013.01);
(Continued)

(58) Field of Classification Search
CPC ................... G01N 33/0018; G01N 2033/0019
See application file for complete search history.

(56) References Cited

U.S. PATENT DOCUMENTS 4,874,524 A * 10/1989 Liapis .................... B01D 15/00
                                                   210/672
6,170,318 B1 * 1/2001 Lewis .................. G01N 27/126
                                                   340/632
(Continued)

FOREIGN PATENT DOCUMENTS

JP          3282586          3/2002
JP        2002-350313        12/2002
(Continued)

OTHER PUBLICATIONS

Extended European Search Report dated Apr. 5, 2018 in Patent Application No. 17192161.2.

*Primary Examiner* — Jill E Culler
*Assistant Examiner* — Ruben C. Parco, Jr.
(74) *Attorney, Agent, or Firm* — Oblon, McClelland, Maier & Neustadt, L.L.P.

(57) ABSTRACT

A molecular detection apparatus according to a embodiment includes: a collection unit which collects detection target gases each containing molecule to be detected; a concentration adjusting unit which dilutes and/or concentrates the molecule, and generates a plurality of detection target gases having different concentrations of the molecule; a detection unit to which the plurality of detection target gases are sequentially introduced, and which includes a plurality of detection cells each outputting detection signals based on the concentrations of the molecule in the plurality of detection target gases; and a discrimination unit which discriminates the molecule by change tendencies of the detection signals based on the concentrations of the molecule.

14 Claims, 9 Drawing Sheets

(51) Int. Cl.
   *G01N 30/54*   (2006.01)
   *G01N 30/70*   (2006.01)
   *G01N 30/02*   (2006.01)

(52) U.S. Cl.
   CPC ... *G01N 33/0031* (2013.01); *G01N 2030/025* (2013.01); *G01N 2033/0019* (2013.01)

(56) References Cited

U.S. PATENT DOCUMENTS

| | | | | |
|---|---|---|---|---|
| 8,373,205 | B2* | 2/2013 | Fleischer | G01N 27/4143 |
| | | | | 257/253 |
| 9,823,211 | B1* | 11/2017 | Allen | G01N 33/0031 |
| 2004/0040841 | A1* | 3/2004 | Gonzalez-Martin | |
| | | | | G01N 33/0031 |
| | | | | 204/406 |
| 2012/0212242 | A1* | 8/2012 | Masel | G01N 27/127 |
| | | | | 324/693 |
| 2013/0273665 | A1 | 10/2013 | Swager et al. | |
| 2014/0309947 | A1 | 10/2014 | Gryska et al. | |
| 2017/0160221 | A1* | 6/2017 | Savoy | G01N 33/0008 |
| 2017/0212069 | A1* | 7/2017 | Nakao | B01J 20/02 |
| 2017/0350854 | A1 | 12/2017 | Yamada et al. | |
| 2018/0059053 | A1 | 3/2018 | Yamada et al. | |

FOREIGN PATENT DOCUMENTS

| | | |
|---|---|---|
| JP | 2010-19688 | 1/2010 |
| JP | 2010-139269 | 6/2010 |
| JP | 5533378 | 5/2014 |
| JP | 3628234 | 12/2014 |
| JP | 2015-500501 A | 1/2015 |
| JP | 2015-515622 | 5/2015 |
| JP | WO2017/042851 A1 | 3/2017 |
| WO | WO 2013/184222 A2 | 12/2013 |
| WO | WO 2017/025996 A1 | 2/2017 |

* cited by examiner

MOLECULAR DETECTION APPARATUS AND MOLECULAR DETECTION METHOD

CROSS REFERENCE TO RELATED APPLICATION

This application is based upon and claims the benefit of priority from Japanese Patent Application No. 2017-054569, filed on Mar. 21, 2017; the entire contents of which are incorporated herein by reference.

FIELD

Embodiments described herein generally relate to a molecular detection apparatus and a molecular detection method.

BACKGROUND

A water heater or the like for household use is provided with an apparatus that detects carbon monoxide generated when incomplete combustion occurs and notifies the risk thereof at an early stage. Such a gas component considerably affects a human body. According to the guidelines from LP gas safety committee, it is set that a carbon monoxide concentration of approximately 200 ppm (parts per million) causes headaches. Although various methods have been known as a method of detecting a gas component having a relatively higher concentration, the detection methods have been limited for detecting the gas component having a concentration in the order of ppb (parts per billion) to ppt (parts per trillion), which corresponds to an extremely low concentration.

At a disaster site or a site at which an act of terrorism occurs or the like, it has been desired to sense the risk in advance by detecting an extremely small amount of the gas component. The gas component having an extremely low concentration is often detected by use of large equipment in research facilities. In this case, a large sized installation type apparatus, which is expensive and has large weight and volume, such as a gas chromatography or a mass spectrometer is required. Under such circumstances, it has been required to provide an apparatus that is capable of detecting the gas component having the extremely low concentration in real time, in other words, an apparatus that has a smaller weight and volume and a better portability and enables selective and higher sensitive detection of the gas component having the extremely low concentration in the order of ppt to ppb.

As a detection element for the gas component having a low concentration, for example, an element has been known that has a conductive layer in which a surface of a carbon nanostructure is surface modified with an organic substance or the like that selectively reacts with or adsorbs a specific substance and outputs a potential difference or the like that changes depending on the gas component that has adhered to the surface of the carbon nanostructure as a detection signal. In such a detection element, there is a possibility that it is impossible to accurately detect a detection target gas component when a component or the like similar to the detection target gas component is mixed in the gas obtained from, for example, the air as impurities. Further, there is a possibility that error occurs in the detection signal resulting from a state of the detection element or the like according to a constitution where the gas obtained from the air is just introduced into a detection unit having the detection element as stated above, because a concentration of a detection target component (gas molecule) in the obtained gas is one point. In such a case, it is difficult to increase detection accuracy of the gas component.

DETAILED DESCRIPTION

According to the embodiments of the present invention, there is provided a molecular detection apparatus that includes: a collection unit which collects detection target gases each containing molecule to be detected; a concentration adjusting unit which dilutes and/or concentrates the molecule to be detected in at least one of the detection target gases collected by the collection unit, and generates a plurality of the detection target gases having different concentrations of the molecule to be detected; a detection unit to which the plurality of detection target gases generated at the concentration adjusting unit are sequentially introduced, and which includes a plurality of detection cells each outputting detection signals based on the concentrations of the molecule to be detected in the plurality of detection target gases; and a discrimination unit which discriminates the molecule to be detected by change tendencies of the detection signals based on the concentrations of the molecule to be detected output from the plurality of detection cells.

Hereinafter, there will be explained a molecular detection apparatus and a molecular detection method according to embodiments with reference to the drawings. In the embodiments, substantially the same constituent elements are denoted by the same reference signs and a description thereof will be omitted in some case. The drawings are schematic, and a relation of the thickness and the planar dimension of each part, a thickness ratio among parts, and so on may differ from actual ones.

Figure 1:
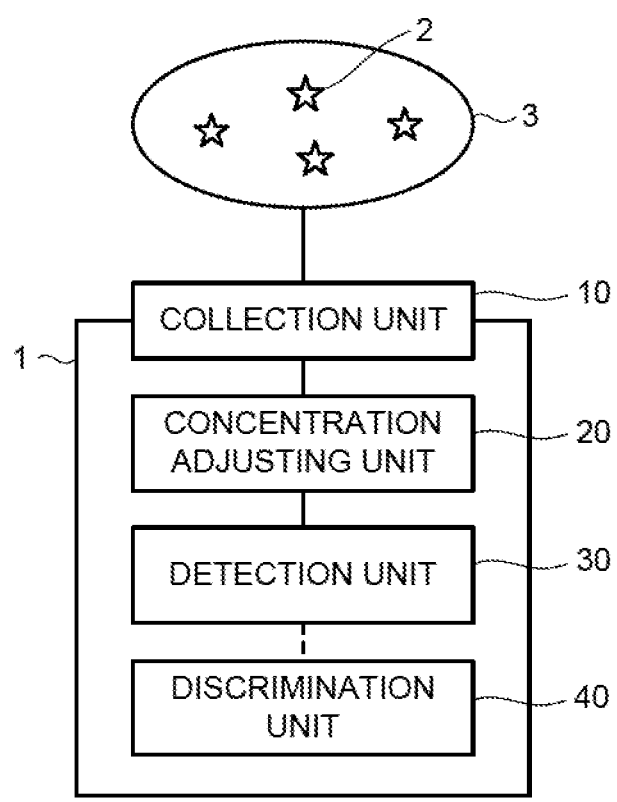
FIG. 1 is a block diagram illustrating a molecular detection apparatus according to an embodiment.

FIG. 1 is a block diagram illustrating a molecular detection apparatus according to the embodiment. A molecular detection apparatus 1 illustrated in FIG. 1 is, for example, an apparatus that detects, from a detection target gas 3 containing molecules to be detected (substances to be detected) 2 generated from a gas generation source, the molecule to be detected 2, and includes a collection unit 10, a concentration adjusting unit 20, a detection unit 30 and a discrimination unit 40. The detection target gas 3 containing the molecules to be detected (gas molecules to be detected) 2 is, first collected by the collection unit 10 in the molecular detection apparatus 1. The collection unit 10 has a collection port for the detection target gas 3 and is connected to the concentration adjusting unit 20 via a gas flow path. The collection unit 10 may include a filter for removing impurities such as fine particles contained in the detection target gas 3.

Figure 2:
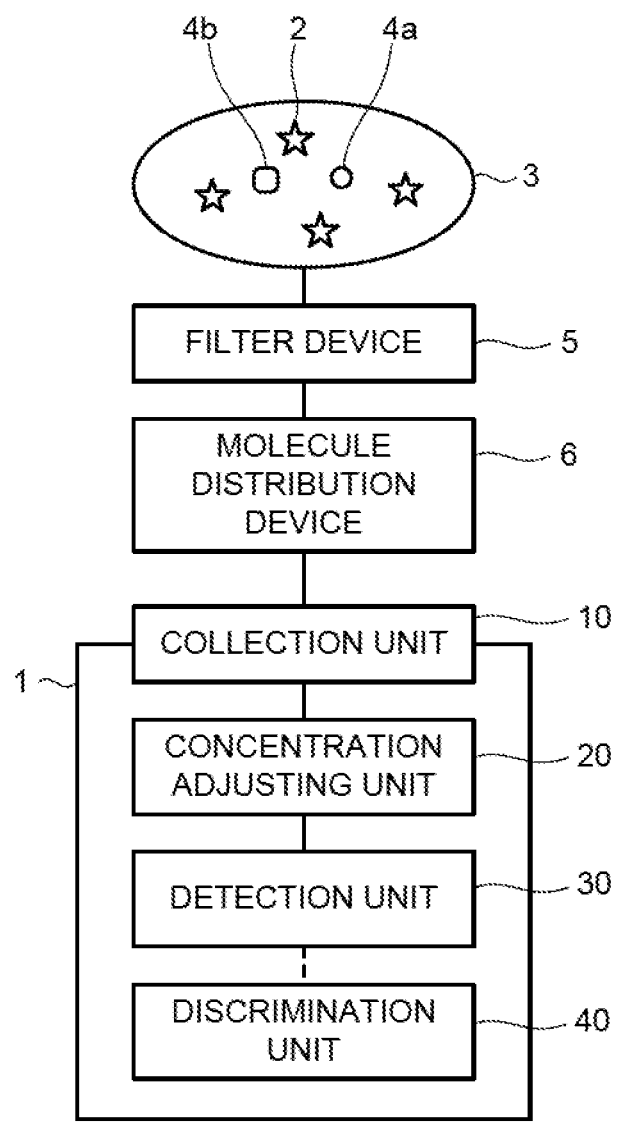
FIG. 2 is a block diagram illustrating a modified example of the molecular detection apparatus illustrated in FIG. 1.

The detection target gas 3 sometimes contains, as impurities, substances having a molecular weight, a molecular structure or the like similar to those of the molecules to be detected 2. Further, as illustrated in FIG. 2, the molecules to be detected 2 drifting in the air often exist in a state where the molecules to be detected 2 are mixed with various foreign substances 4 (4a and 4b) such as odor components and fine particles. From those perspectives, as illustrated in FIG. 2, the detection target gas 3 may be sent to the molecular detection apparatus 1 after being preprocessed by a filter device 5, a molecular distribution device 6, and the like beforehand.

For the filter device 5 out of the devices of preprocess, a generally-used moderate-to-high performance filter or the like is used. The filter device 5 removes particulate substances such as fine particles contained in the detection target gas 3. The detection target gas 3, from which the particulate substances are removed in the filter device 5, is then sent to the molecular distribution device 6. As the molecular distribution device 6, there can be cited, for example, an apparatus that ionizes the detection target gas 3 to form an ionized substance group, applies voltage to the ionized substance group to allow the ionized substance group to fly at a speed proportional to the mass thereof, and separates an ionized substance of the molecule to be detected 2 from the ionized substance group using a flight speed based on the difference in mass and a time of flight based on the flight speed. As the molecular distribution device 6 as above, a device or the like including an ionization unit, a voltage application unit, and a time-of-flight separation unit is used.

The detection target gas 3 containing the molecules to be detected 2 is collected by the collection unit 10 directly, or after being preprocessed by the devices such as the filter device 5 and the molecular distribution device 6. The detection target gas 3 containing molecules to be detected 2 collected by the collection unit 10 is then sent to the concentration adjusting unit 20. The concentration adjusting unit 20 generates a plurality of detection target gases 3 having different concentrations of the molecule to be detected 2 by diluting and/or concentrating the molecule to be detected in the detection target gas 3 collected by the collection unit 10. The detection target gas 3 collected by the collection unit 10, that is the detection target gas 3 whose concentration of the molecule to be detected 2 is not diluted or concentrated, is included in the plurality of detection target gases 3 having different concentrations. The concentration adjusting unit 20 as stated above is intervened between the collection unit 10 and the detection unit 30, and thereby, the plurality of detection target gases 3 having different concentrations of the molecule to be detected 2 are sent to the detection unit 30. At the detection unit 30, the detections of the molecules to be detected 2 having different concentrations in the plurality of detection target gases 3 are performed. It is thereby possible to obtain correlation of detection signals with respect to the concentrations of the molecule to be detected 2 at the detection unit 30.

Figure 3:
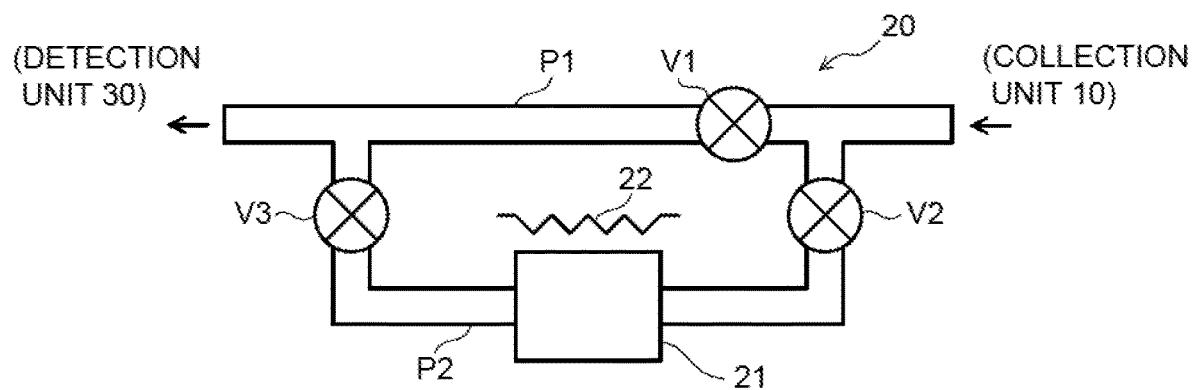
FIG. 3 is a view illustrating a concentration adjusting unit in the molecular detection apparatus according to the embodiment.

A configuration of the concentration adjusting unit 20 is not particularly limited as long as it possible to dilute and/or concentrate the molecule to be detected 2 in the detection target gas 3, and to thereby generate the plurality of detection target gases 3 having different concentrations of the molecule to be detected 2. FIG. 3 illustrates an example of the configuration of the concentration adjusting unit 20. The concentration adjusting unit 20 illustrated in FIG. 3 includes an adsorber 21 that adsorbs the molecules to be detected 2 and a heater 22 that heats the adsorber 21. As the adsorber 21, an adsorber is used where an adsorbent capable of adsorbing and desorbing the molecules to be detected 2, for example, an organic adsorbent such as Tenax (registered trademark, manufactured by Toho Tenax Co., Ltd.) and an inorganic adsorbent such as a carbon adsorbent is filled in a glass tube or the like. The heater 22 heats the adsorber 21 that adsorbs the molecules to be detected 2, and it is used to reproduce the adsorber 21 by desorbing the molecules to be detected 2 from the adsorbent, or to generate the detection target gas 3 which is concentrated by desorbing the molecules to be detected 2 from the adsorbent.

When the detection target gas 3 sent to the concentration adjusting unit 20 passes through the adsorber 21, the molecules to be detected 2 in the detection target gas 3 are adsorbed by the adsorber 21. The detection target gas 3 from which the molecules to be detected 2 are adsorbed is mixed with the detection target gas 3 containing the molecules to be detected 2 which is sent from the collection unit 10, and thereby, the detection target gas 3 where the molecule to be detected 2 is diluted can be obtained. At this time, if the adsorber 21 can adsorb only a part of the molecules to be detected 2, the detection target gas 3 where the molecule to be detected 2 is diluted can be generated by passing the detection target gas 3 through the adsorber 21. The detection target gas 3 where the molecule to be detected 2 is concentrated can be generated by desorbing the molecules to be detected 2 from the adsorber 21 adsorbing the molecules to be detected 2.

A concrete configuration of the concentration adjusting unit 20 and a procedure to dilute and/or concentrate the molecule to be detected 2 using the concentration adjusting unit 20 are described with reference to FIG. 3 to FIG. 6. The concentration adjusting unit 20 illustrated in FIG. 3 to FIG. 6 includes a first gas flow path P1 that directly sends the detection target gas 3 containing the molecules to be detected 2 from the collection unit 10 to the detection unit 30 and a second gas flow path P2 that is branched off from a middle of the first gas flow path P1 and is equipped with the adsorber 21. The concentration adjusting unit 20 further includes the heater 22 that heats the adsorber 21 to desorb the adsorbed molecules to be detected 2. Both ends of the second gas flow path P2 are connected to the first gas flow path P1. In the second gas flow path P2, the detection target gas 3 containing the molecules to be detected 2 is sent from the collection unit 10 to the detection unit 30 through the adsorber 21. The first gas flow path P1 includes a first valve V1. The second gas flow path P2 includes a second valve V2 and a third valve V3 disposed in front and in rear of the adsorber 21.

Figure 4:
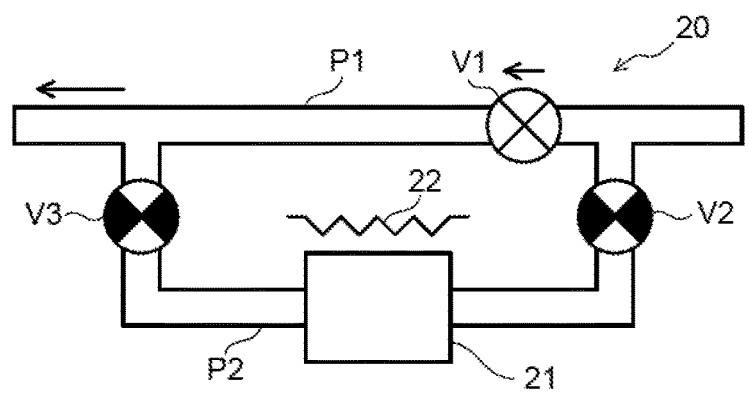
FIG. 4 is a view to explain operations of the concentration adjusting unit illustrated in FIG. 3.

FIG. 4 illustrates a state where the detection target gas 3 collected at the collection unit 10 is sent to the detection unit 30 without being diluted and concentrated. That is, the first valve V1 provided at the first gas flow path P1 is set to be opened, the second and third valves V2, V3 provided at the second gas flow path P2 are set to be closed, and thereby, the detection target gas 3 collected at the collection unit 10 is directly sent to the detection unit 30 without being diluted and concentrated. The detection target gas 3 at a certain flow rate is sent under this state to the concentration adjusting unit 20, and thereby, the detection target gas 3 containing the molecules to be detected 2 having a first concentration can be sent to the detection unit 30.

Figure 5:
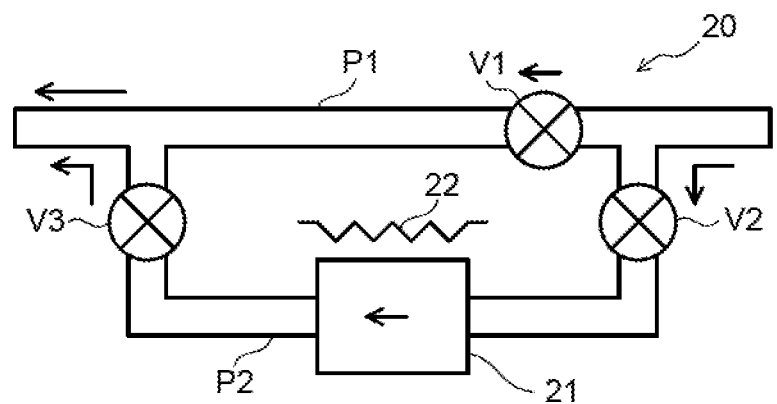
FIG. 5 is a view to explain the operations of the concentration adjusting unit illustrated in FIG. 3.

FIG. 5 illustrates an example of a state where the detection target gas 3 collected at the collection unit 10 is diluted and sent to the detection unit 30. That is, the first valve V1 provided at the first gas flow path P1 is set to be opened, the second and third valves V2, V3 provided at the second gas flow path P2 are set to be opened, and thereby, a part of the detection target gas 3 collected at the collection unit 10 is sent to the detection unit 30 by passing through the adsorber 21, and another part of the detection target gas 3 is sent to the detection unit 30 without passing through the adsorber 21. The second gas flow path P2 is merged with the first gas flow path P1 at a front stage of the detection unit 30. Accordingly, the detection target gas 3 where the molecules to be detected 2 are adsorbed at the adsorber 21 is mixed with the detection target gas 3 passing through the first gas flow path P1, and thereby, it is possible to generate the detection target gas 3 where the molecule to be detected 2 is diluted.

Here, the detection target gas 3 at the certain flow rate is sent to the concentration adjusting unit 20 under this state, and thereby it is possible to send the detection target gas 3 having a second concentration where the molecule to be detected 2 is diluted to the detection unit 30. A merging part of the second gas flow path P2 with the first gas flow path P1 functions as a mixing part of the detection target gas 3 from which the molecules to be detected 2 are adsorbed with the detection target gas 3 passing through the first gas flow path P1. Further, a flow rate control valve or the like is provided at each of the first and second gas flow paths P1, P2 to thereby adjust a mixing ratio between the detection target gas 3 flowing through the first gas flow path P1 and the detection target gas 3 flowing through the second gas flow path P2 to make a degree of dilution different, and thereby, it is also possible to obtain a plurality of detection target gases 3 having different concentrations of the diluted molecule to be detected 2.

Note that when the adsorber 21 that adsorbs only a part of the molecules to be detected 2 is used, the first valve V1 provided at the first gas flow path P1 is set to be closed, and the second and third valves V2, V3 provided at the second gas flow path P2 are set to be opened, and thereby, it is possible to pass the detection target gas 3 collected at the collection unit 10 through the adsorber 21, and to adsorb only a part of the molecules to be detected 2 in the detection target gas 3 at the adsorber 21. Accordingly, the detection target gas 3 passing through the adsorber 21 is in a state where the molecule to be detected 2 is diluted. The detection target gas 3 at the certain flow rate is sent to the concentration adjusting unit 20 under this state, and thereby, the detection target gas 3 having the second concentration where the molecule to be detected 2 is diluted can be sent to the detection unit 30.

Figure 6:
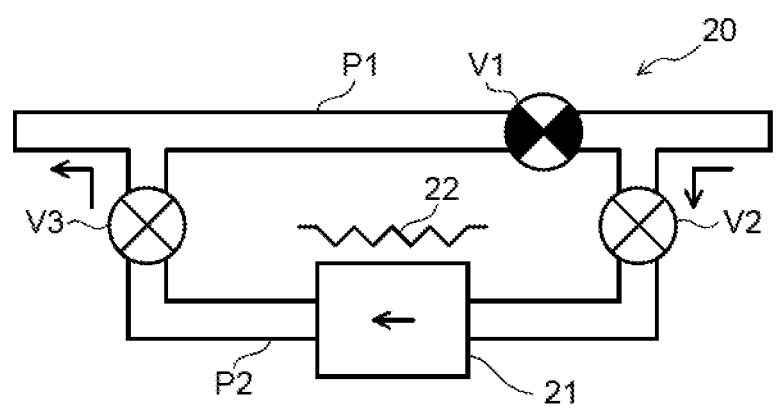
FIG. 6 is a view to explain the operations of the concentration adjusting unit illustrated in FIG. 3.

FIG. 6 illustrates an example of a state where the detection target gas 3 collected at the collection unit 10 is concentrated and sent to the detection unit 30. A device capable of adsorbing the molecules to be detected 2 in the detection target gas 3 and desorbing the molecules to be detected 2 by being heated is used as the adsorber 21. First, the first valve V1 provided at the first gas flow path P1 is set to be closed, the second and third valves V2, V3 provided at the second gas flow path P2 are set to be opened, to thereby pass the detection target gas 3 collected at the collection unit 10 through the adsorber 21. The molecules to be detected 2 in the detection target gas 3 are adsorbed by the adsorber 21. After some amount of molecules to be detected 2 are adsorbed by the adsorber 21, the second valve V2 is set to be closed, then the adsorber 21 is heated by the heater 22 to thereby desorb the molecules to be detected 2. Thus, the detection target gas 3 having a third concentration where the molecule to be detected 2 is concentrated can be sent to the detection unit 30. At this time, the second valve V2 may be set to be opened, to send the detection target gas 3 to the concentration adjusting unit 20 instead of carrier gas. Further, it is also possible to obtain the plurality of detection target gases 3 having different concentrations of the concentrated molecule to be detected 2 by adjusting the amount of the molecules to be detected 2 adsorbed by the adsorber 21 to thereby change a degree of concentration.

As stated above, the concentration adjusting unit 20 which includes the first gas flow path P1 directly sending the detection target gas 3 from the collection unit 10 to the detection unit 30 and the second gas flow path P2 including the adsorber 21 capable of adsorbing and desorbing the molecules to be detected 2 is used, and thereby, it is possible to generate the detection target gas 3 having the concentration (first concentration) of the molecule to be detected 2 in the state as it is collected by the collection unit 10, the detection target gas 3 having the concentration (second concentration) which is diluted by adsorbing the molecules to be detected 2 by the adsorber 21, and the detection target gas 3 having the concentration (third concentration) which is concentrated by heating the adsorber 21 to desorb the molecules to be detected 2. The plurality of detection target gases 3 having different concentrations of the molecule to be detected 2 are sequentially sent to the detection unit 30, and thereby, it is possible to obtain correlation of detection signals with respect to the concentrations of the molecule to be detected 2 at the detection unit 30. At least there may be two kinds of detection target gases 3 having different concentrations of the molecule to be detected 2, and there is preferably three kinds or more. It is possible to generate four or more kinds of detection target gases 3 by adjusting a dilution degree and a concentration degree.

Figure 7:
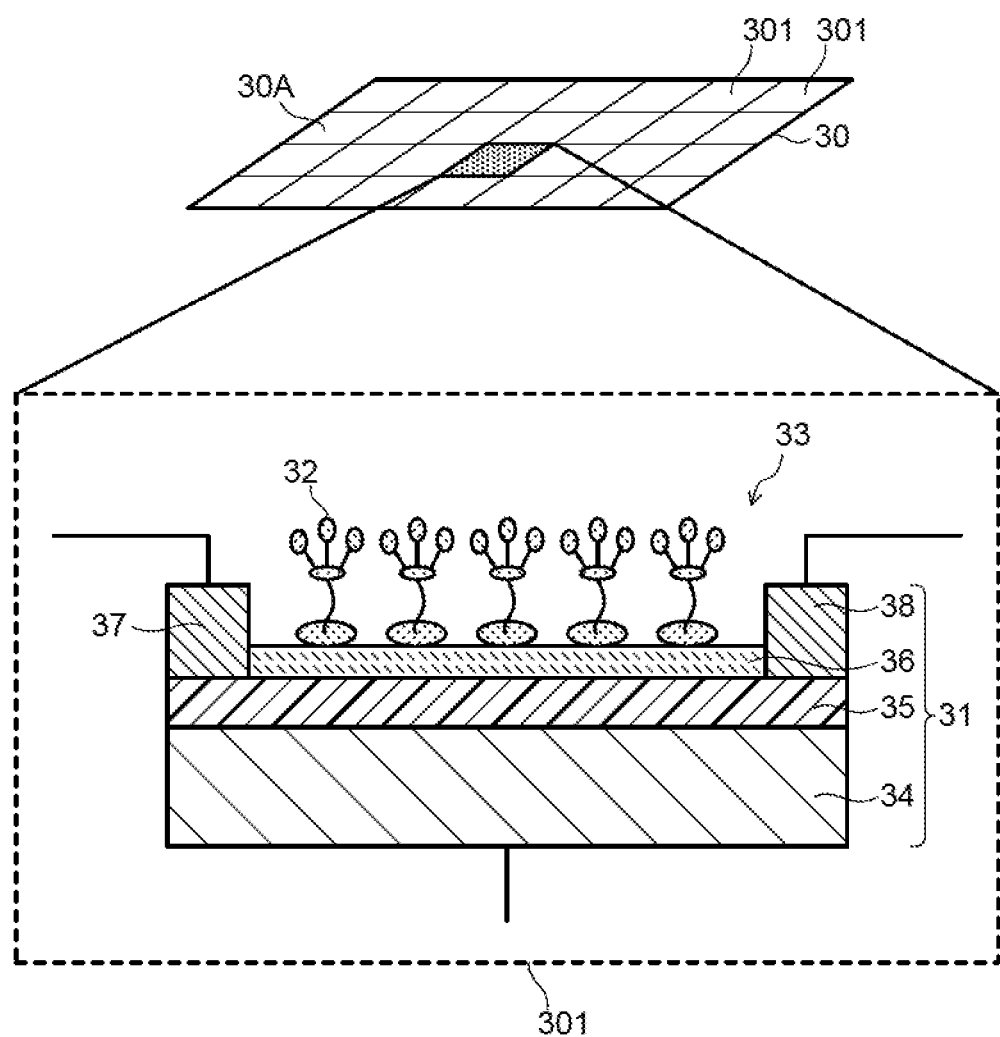
FIG. 7 is a view illustrating a detection unit in the molecular detection apparatus according to the embodiment.

The plurality of detection target gases 3 having different concentrations of the molecule to be detected 2 which are adjusted by the concentration adjusting unit 20 are sequentially sent to the detection unit 30. The detection unit 30 is constituted to output the detection signals based on the concentrations of the molecule to be detected 2 in the plurality of detection target gases 3. The detection unit 30 includes a detection surface 30A sectioned into a plurality of detection cells 301 as illustrated in FIG. 7. The detection surface 30A of the detection unit 30 is disposed to face a gas outlet port of the first gas flow path P1 of the concentration adjusting unit 20. The plurality of detection cells 301 each include a detection element 33 having a sensor unit 31 and organic probes 32 provided at the sensor unit 31. FIG. 7 illustrates the detection element 33 where a graphene field effect transistor (GFET) is used for the sensor unit 31. Note that the sensor unit 31 is not limited to the GFET, but may be a sensor using a carbon nanostructure such as a carbon nanotube.

The GFET serving as the sensor unit 31 includes a semiconductor substrate 34 that functions as a gate electrode, an insulating film 35 provided as a gate insulating layer on the semiconductor substrate 34, a graphene layer 36 provided as a channel on the insulating film 35, a source electrode 37 provided at one end of the graphene layer 36, and a drain electrode 38 provided at the other end of the graphene layer 36. The organic probes 32 are provided on the graphene layer 36 of the GFET 31. The molecules to be detected 2 that are led into the detection unit 30 are captured by the organic probes 32 provided on the graphene layer 36. Electron transfer or the like occurs from the molecule to be detected 2 captured by the organic probe 32 to the GFET 31, thereby electrical change generated at the sensor unit 31 is output as the detection signal. In this way, the target molecule to be detected 2 is selectively detected.

An organic matter forming the organic probe 32 has a property of dissolving in a solvent. Thus, the organic probe 32 can be installed at the graphene layer 36 by applying a solution obtained by dissolving the organic matter in a solvent to the graphene layer 36. In order to easily obtain an interaction with graphene, the organic probe 32 preferably has a portion having such a structure as a pyrene ring. A molecule having such a structure as the pyrene ring interacts with a hexagonally shaped π electron system formed by carbon of the graphene, and forms an interaction state of what is called π-π stacking. Low-concentration probe molecules are dissolved in a solvent and the resultant is applied to the graphene, and thereby the π-π stacking is formed between the pyrene ring and the graphene and the probe molecules are aligned on the graphene to be fixed. By using such a self-alignment action, the organic probe 32 can be installed on the graphene layer 36.

When the molecules to be detected 2 are captured by the organic probes 32 provided on the graphene layer 36, an output from the GFET 31, for example, a drain current value changes. The case of a single layer of graphene means that there is zero gap, and thus, the source electrode 37 and the drain electrode 38 are continuously electrified normally. When the number of graphene layers increases to two or three layers, a band gap is generated, but such a band gap in an actual system is relatively smaller than that considered from a strict theoretical value. When the gate insulating layer 35 has a dielectric constant approximately similar to that of a silicon oxide film, the source electrode 37 and the drain electrode 38 are often continuously electrified. Thus, the graphene layer 36 may be formed of a stack composed of about five graphene layers or less as well as the single layer structure of graphene.

The molecule to be detected 2 flying in the vicinity of the organic probe 32 is attracted to the organic probe 32 by hydrogen bonding force or the like, or comes into contact with the organic probe 32 in some cases. When the contact with the molecule to be detected 2 occurs, an interchange of electrons occurs between the molecule to be detected 2 and the organic probe 32, and the organic probe 32 transmits an electrical change to the graphene layer 36 being in contact therewith. The electrical change transmitted from the organic probe 32 to the graphene layer 36 disturbs the flow of electricity between the source electrode 37 and the drain electrode 38, and thus the GFET 31 functions as a sensor.

With the GFET 31 using the graphene layer 36 as a channel, even an extremely slight electrical change appears significantly as an output. As a result, it is possible to constitute the highly sensitive detection element 33. The sensor using the GFET 31 also has a tendency that electric current flows between the source electrode 37 and the drain electrode 38 without application of voltage to the gate electrode 34 because the graphene has a property as a zero-gap semiconductor. Thus, the GFET 31 functions as a sensor as it is. However, normally, the GFET 31 applies electric current between the source electrode 37 and the drain electrode 38 in a state of applying voltage to the gate electrode 34, and observes an electrical change of the gate electrode 34 when the organic probe 32 captures the molecule to be detected 2, a change of a drain current, and so on.

In the detection of the molecule to be detected 2 performed by the above-described detection element 33, as the transfer of electrons from the molecule to be detected 2 that is captured by the organic probe 32 to the GFET 31 is higher, the function as the sensor is further increased. The sensor using the GFET 31 is regarded as the most sensitive FET sensor, and can improve sensitivity about three times as compared to a sensor using a carbon nanotube. Thus, using the detection element 33 in which the GFET 31 and the organic probe 32 are combined enables higher sensitive detection of the molecule to be detected 2.

FIG. 7 illustrates the detection surface 30A on which the plurality of detection cells 301 are arranged in a grid pattern (an array pattern), but is not necessarily limited thereto. The plurality of detection cells 301 may be arranged linearly. At least some of the organic probes 32 provided at the graphene layers 36 of the plurality of detection cells 301 are different in bond strength with the molecule to be detected 2, in the electrical change when they are bonded to the molecule to be detected 2, and so on. That is, the plurality of detection cells 301 include a plurality of the organic probes 32 different in the bond strength with the molecule to be detected 2, the electrical change based on them, and so on. All the organic probes 32 may be different in the bond strength with the molecule to be detected 2, the electrical change based on them, and so on, or some of the organic probes 32 may be different in the bond strength with the molecule to be detected 2, the electrical change based on them, and so on. Note that a density of the organic probes 32 on the graphene layer 36 may be changed instead of providing the organic probes 32 which are different in the bond strength with the molecule to be detected 2, the electrical change based on them, and so on.

Figure 8:
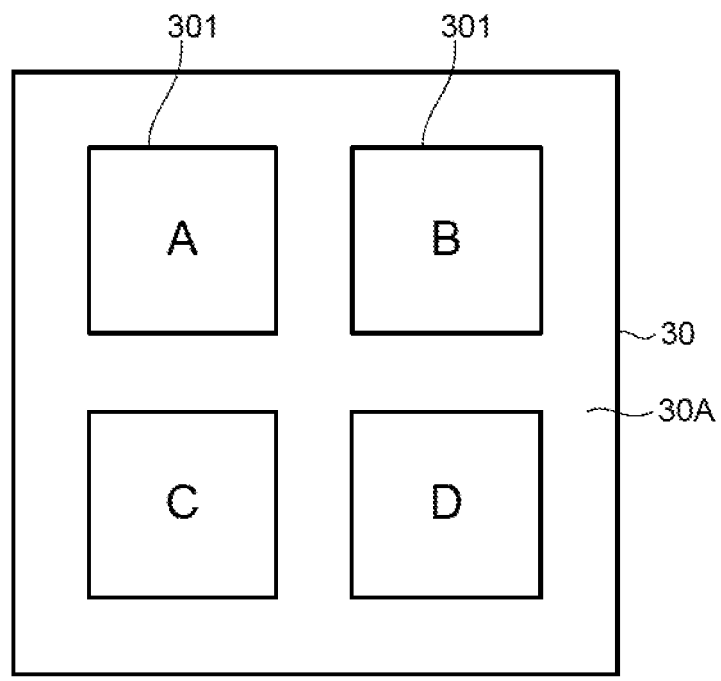
FIG. 8 is a view illustrating an example of detection cells according to the embodiment.

FIG. 8 illustrates a grid-shaped sensor in which the detection surface 30A of the detection unit 30 is sectioned into four detection cells 301, that is a detection cell A, a detection cell B, a detection cell C, and a detection cell D. At least some of the detection cells A to D, different kinds of organic probes 32, that is the plurality of organic probes 32 different in the bond strength with the molecule to be detected 2, the electrical change based on them, and so on, are provided. The plurality of organic probes 32 each have an interaction with the molecule to be detected 2, but are different in working strength (the bond strength) with the molecule to be detected 2, the electrical change based on them, and so on, and thus intensities of the detection signals, correlations of the detection signals with respect to the concentrations of the molecule to be detected 2, and so on are different.

Figure 9:
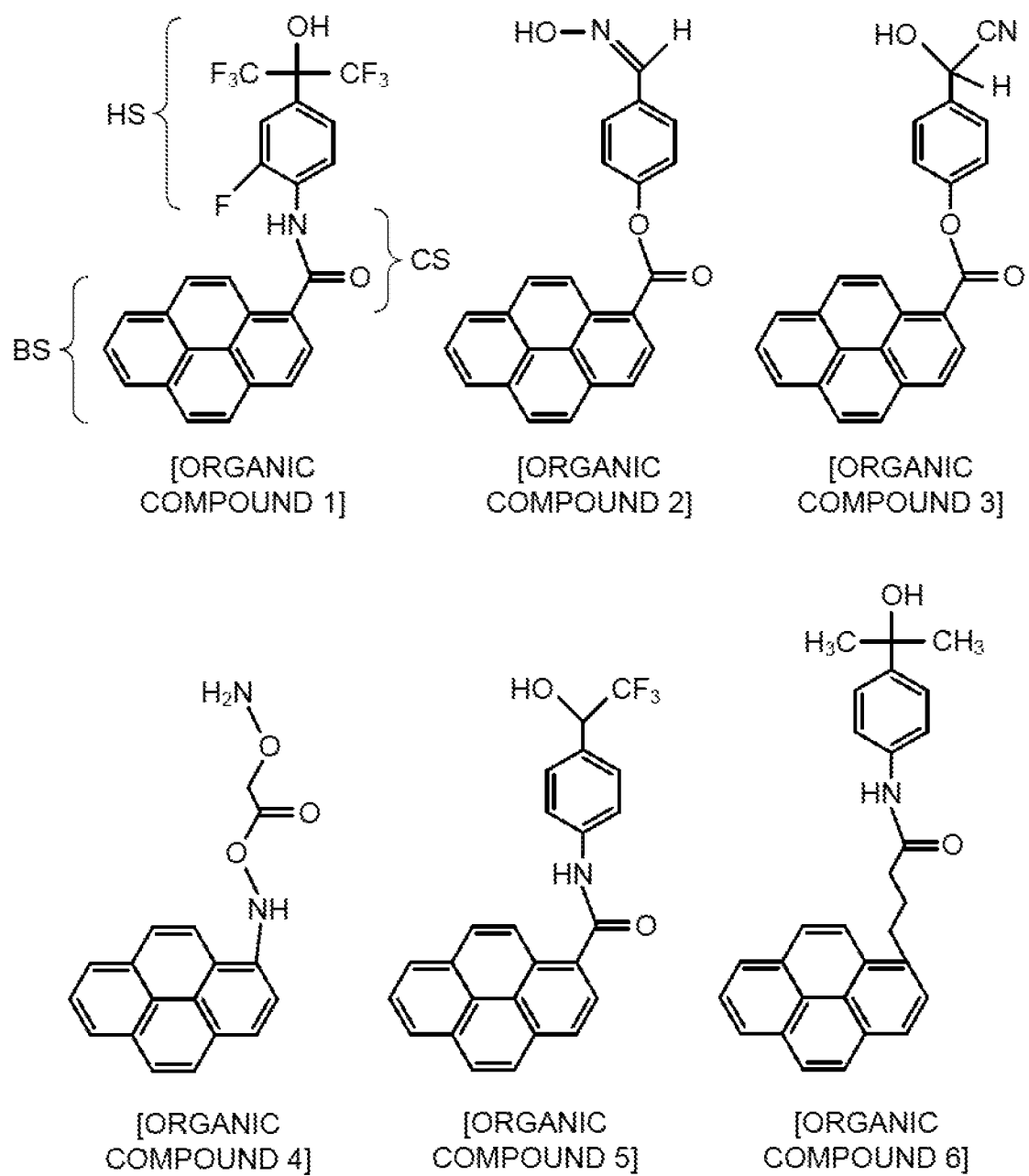
FIG. 9 is a view illustrating examples of organic compounds used for organic probes according to the embodiment.

FIG. 9 illustrates examples of the organic probes 32 provided on the graphene layer 36 of each of the detection cells A to D. Among organic compounds each forming the organic probe 32, organic compounds 1 to 3, 5 to 6 each have a hydroxy group (—OH) as a reactive group with respect to the molecule to be detected 2. An organic compound 4 has an amino group (—NH$_2$) as the reactive group. However, only the reactive group hardly reacts with the gas component. Thus, for the purpose of enhancing a hydrogen bonding property, an organic compound where a functional group (neighboring group) excellent in an inductive effect is introduced to a neighboring portion of the reactive group is used.

As the neighboring group with respect to the hydroxy group (—OH) being the reactive group, there can be cited an alkyl group wind is substituted by fluorine atoms such as a trifluoromethyl group (—CF$_3$) and a hexafluoroethyl group (—C$_2$F$_5$), a functional group containing nitrogen such as a cyano group (—CN), a nitro group (—NO$_2$) and a —CHN group, and the alkyl group such as a methyl group (—CH$_3$) and an ethyl group (—C$_2$H$_5$). The organic compounds 1, 5 have the trifluoromethyl group (—CF$_3$) as the neighboring group of the reactive group (—OH). The organic compound 2 has a —CHN—OH group as the functional group containing the reactive group. The organic compound 3 has the cyano group (—CN) as the neighboring group of the reactive group (—OH). The organic compound 6 has the methyl group (—CH$_3$) as the neighboring group of the reactive group (—OH). As the neighboring group with respect to the amino group (—NH$_2$) being the reactive group, there can be cited an ether linkage group (—O—). The organic compound 4 has a —O—NH$_2$ group as the functional group containing the reactive group.

The organic compounds 1 to 6 illustrated in FIG. 9 are examples of the organic compounds each forming the organic probe 32, and the organic probe 32 is not limited to the organic compounds 1 to 6. As illustrated in the organic compound 1 in FIG. 9, the organic probe 32 is preferably formed of an organic compound that has a head portion HS having the reactive group such as the hydroxy group and the amino group and the above-stated neighboring group, a base portion BS serving as an installation portion for the graphene layer 36 or the like, and a connecting portion CS connecting the head portion HS and the base portion BS. The head portion HS is preferably a monovalent aromatic hydrocarbon group having the reactive group and the neighboring group, and more preferably a phenyl group having the alkyl group (carbon number: approximately 1 to 5) where the reactive group and the neighboring group are bonded to the same carbon.

The base portion BS is preferably a monovalent substituted or unsubstituted polycyclic aromatic hydrocarbon group having a polycyclic structure such as the pyrene ring, an anthracene ring, a naphthacene ring, or a phenanthrene ring, and more preferably a substituted or unsubstituted pyrene group. The connecting portion CS is a bivalent group, and it may be an alkylene group such as a methylene group or au ethylene group, or may be an ether bond (—O—), an ester, bond (—C(=O)O—), a carbonyl bond (—CO—), an amide bond (—NH—CO—), an imide bond (—CO—NH—CO—), and so on. Besides, the head portion HS and the base portion BS may be directly bonded.

In the above-stated organic compound forming the organic probe 32, it is possible to adjust the bond strength with the molecule to be detected 2, an electron transfer state with the molecule to be detected 2, and so on by changing the kind of the reactive group, the kind and the number of neighboring groups with respect to the reactive group, and so on. For example, the neighboring group (CH$_3$ group) of the organic compound 6 is different in kind from the neighboring group (CF$_3$ group) of the organic compound 1. The trifluoromethyl group has a large effect of enhancing activity of the reactive group (OH group) owing to fluorine having high electronegativity, though such effect of the methyl group is small. It is therefore possible to make the bond strength with the molecule to be detected 2 or the like different. The number of neighboring groups (CF$_3$ group) of the organic compound 5 is different from that of the organic compound 1, and therefore, they are different in the bond strength with the molecule to be detected 2. The kind of the functional group containing the reactive group of each of the organic compounds 2 to 4 is different from that of the organic compound 1, and therefore, they are different in the bond strength with the molecule to be detected 2 or the like.

As stated above, the bond strength with the molecule to be detected 2, the electron transfer state with the molecule to be detected 2, the electrical change based on them and so on are adjusted in accordance with the kinds of organic compound forming the organic probe 32. Besides, a relationship with the molecule to be detected 2 can be adjusted by the density of the organic probes 32 provided on the detection cell 301, or by using the plurality of organic probes 32 to be mixed and adjusting a mixture ratio or the like at that time. The correlations of the detection signals from the detection cells A to D with respect to the concentration of the molecule to be detected 2 are different based on the differences in the bond strength of the organic probe 32 with the molecule to be detected 2 and in the electron transfer state or the like between the organic probe 32 and the molecule to be detected 2. For example, change tendencies of the detection signal are different when the concentration of the molecule to be detected 2 in the detection target gas 3 is changed by changing the kind, the installation density, and so on of the organic probes 32.

Figure 10:
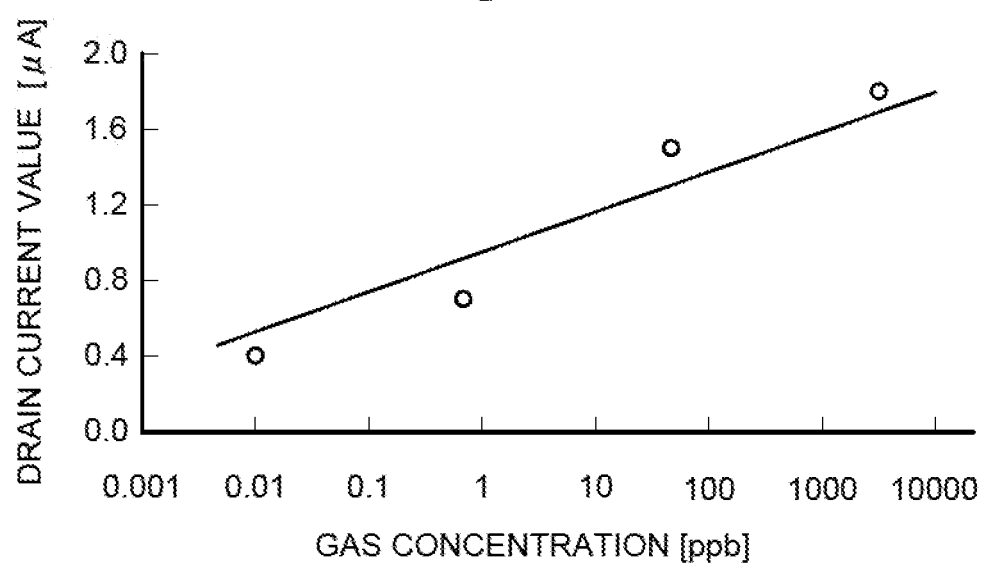
FIG. 10 is a view illustrating an example of a detection result by detection unit the according to the embodiment.
Figure 11:
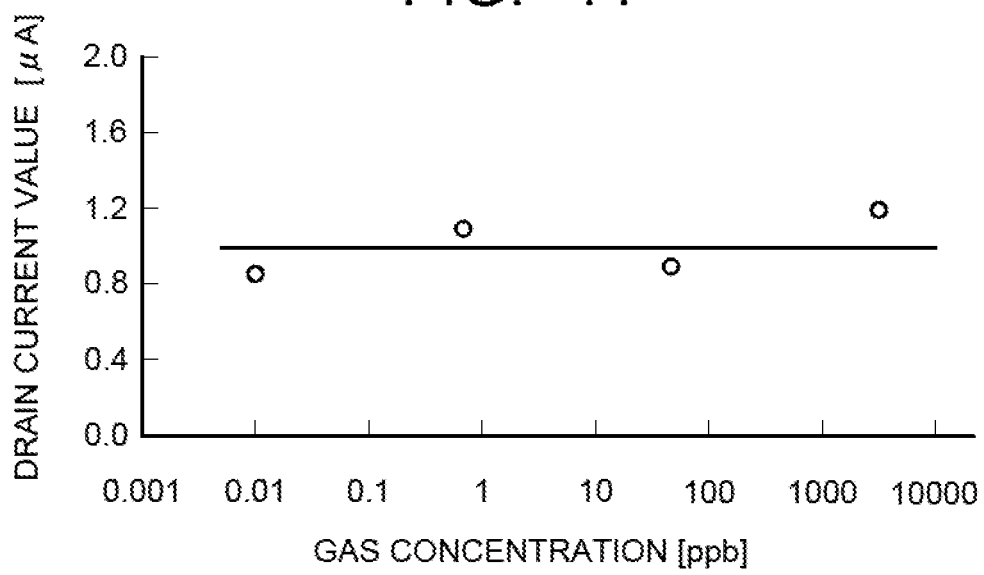
FIG. 11 is a view illustrating another example of a detection result by the detection unit according to the embodiment.
Figure 12:
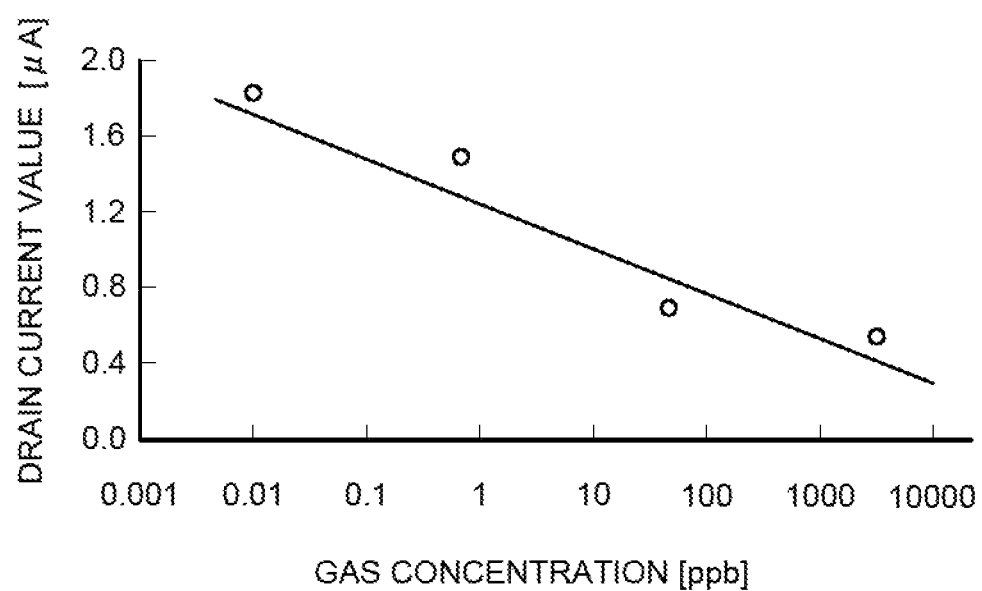
FIG. 12 is a view illustrating the other example of a detection result by the detection unit according to the embodiment.

Typical examples of the change tendencies of the detection signal when the concentration of the molecule to be detected 2 in the detection target gas 3 is changed are illustrated in FIG. 10 to FIG. 12. FIG. 10 to FIG. 12 each illustrate a change of the drain current of the detection element 33 where the GFET is used as the sensor unit 31, as the detection signal of the detection cell 301. FIG. 10 illustrates the example where the detection signal (drain current value) also increases as the concentration of the molecule to be detected 2 increases. FIG. 11 illustrate the example where the detection signal (drain current value) seldom changes even if the concentration of the molecule to be detected 2 increases. FIG. 12 illustrates the example where the detection signal (drain current value) conversely decreases when the concentration of the molecule to be detected 2 increases. As illustrated in FIG. 10 to FIG. 12, the change tendencies of the detection signal based on the concentration of the molecule to be detected 2 are different depending on the kind or the like of the organic probe 32 applied to the detection cell 301. The molecule to be detected 2 can be discriminated by detecting the change tendency of the detection signal based on the concentration of the molecule to be detected 2 as stated above.

The signals detected in the detection cells A to D are sent to the discrimination unit 40 to be signal-processed. For example, the discrimination unit 40 first detects a first detection target gas 3 containing the molecule to be detected 2 with the first concentration to thereby store intensity of a first detection signal output from each of the detection cells A to D. Next, the discrimination unit 40 detects a second detection target gas 3 containing the molecule to be detected 2 with the second concentration where the molecule to be detected 2 is more diluted than the first detection target gas 3, to thereby store intensity of a second detection signal output from each of the detection cells A to D. Further, the discrimination unit 40 detects a third detection target gas 3 containing the molecule to be detected 2 with the third concentration where the molecule to be detected 2 is more concentrated than the first detection target gas 3, to thereby store intensity of a third detection signal output from each of the detection cells A to D. At least either one of the second detection signal or the third detection signal may be stored, but it is more preferable to store both detection signals.

At this time point, though the concrete concentration of the molecule to be detected 2 is not clear when the first to third detection signals are detected, it is known that the second detection signal is a detection signal at a lower concentration side than the first detection signal, and the third detection signal is a detection signal at a higher concentration side than the first detection signal. Accordingly, there is analyzed the correlation (change tendency) between the concentration of the molecule to be detected 2 and the detection signal is analyzed by each of the detection cells A to D based on the first to third detection signals output from each of the detection cells A to D, that is, it is analyzed which correlation between the concentration and the detection signal is formed from among the correlations illustrated in FIG. 10 to FIG. 12. The correlation (change tendency) between the concentration of the molecule to be detected 2 and the detection signal is analyzed by each of the detection cells A to D as described below. For example, in the detection cell A, the detection signal intensity increases in accordance with the increase in the concentration of the molecule to be detected 2. In the detection cell B, the detection signal intensity increases in accordance with the increase in the concentration of the molecule to be detected 2. In the detection cell C, the detection signal intensity decreases in accordance with the increase in the concentration of the molecule to be detected 2. In the detection cell D, the detection signal intensity seldom changes even if the concentration of the molecule to be detected 2 increases.

The correlation between the concentration of the molecule to be detected 2 and the detection signal is stored in the discrimination unit 40 by each of the detection cells A to D in accordance with a substance to be detected. The stored correlation with the detection signal and a detected correlation between the concentration and the detection signal are compared by each of the detection cells A to D, and thereby, the discrimination of the molecule to be detected 2 detected at the detection unit 30 is performed. Types of correlation between the concentration and the detection signal used for the discrimination of the molecule to be detected 2 are not limited to simple change tendencies as illustrated in FIG. 10 to FIG. 12 such that the detection signal intensity simply increases, decreases, or seldom changes in accordance with the increase in the concentration of the molecule to be detected 2. For example, a rate of change of the detection signal intensity in accordance with the increase in the concentration of the molecule to be detected 2, that is, a rate of increase and a rate of decrease may be taken into account.

For example, when the detection signal intensities of both of the detection cell A and the detection cell B increase in accordance with the increase in the concentration of the molecule to be detected 2 where the rates of increase of the detection cells A, B in the detection signal intensity are different with respect to the increase in the concentration, specifically, when the rate of increase of the detection signal intensity of the detection cell A is larger than that of the detection cell B with respect to the same increase in concentration, it is possible to use the difference in the rates of increase of the detection signal intensity between the detection cells A, B for the discrimination of the molecule to be detected 2. It is the same when the detection signal intensity decreases with respect to the increase in the concentration of the molecule to be detected 2, and it is possible to use the difference in the rates of decrease of the detection signal intensity with respect to the increase in the concentration of the molecule to be detected 2 for the discrimination of the molecule to be detected 2. As stated above, the differences in the rates of increase and the rates of decrease of the detection signal intensity with respect to the increase in the concentration of the molecule to be detected 2 are used for the discrimination of the molecule to be detected 2, and thereby, it becomes possible to more accurately discriminate the molecule to be detected 2 by the plurality of detection cells A to D.

As stated above, the change tendencies such that the detection signal intensity of each of the plurality of detection cells A to D increases, decreases, or seldom changes based on the concentration difference of the molecule to be detected 2 in the plurality of detection target gases 3 are used for the discrimination of the molecule to be detected 2, and thereby, it becomes possible to accurately discriminate the molecule to be detected 2. Accordingly, it becomes possible to selectively and highly sensitively detect the gas component (molecule to be detected 2) having an extremely low concentration in the order of ppt to ppb. For example, when the molecule to be detected 2 is discriminated by using the intensity difference (a signal intensity difference as an absolute value) of the detection signals among the detection elements 33 in the plurality of detection cells 301 based on the concentration of the molecule to be detected 2 in one detection target gas 3, there is a possibility that the discrimination accuracy of the molecule to be detected 2 is lowered due to a device-specific variation or the like of the detection element 33. On the other hand, the change tendency of the detection signal based on the concentration difference of the molecule to be detected 2 is used for the discrimination of the molecule to be detected 2, and thereby, it becomes possible to accurately discriminate the molecule to be detected 2 without being influenced by the device-specific variation (variation of the absolute value) or the like of the detection element 33.

The above-stated discrimination method based on the change tendency of the detection signal depending on the concentration change is applied, thereby, it is possible to selectively and highly sensitively detect and discriminate the molecule to be detected 2 even in a case when impurities are mixed in the detection target gas 3 which is led to the detection unit 30. For example, in the case when the molecule to be detected 2 is dimethyl methylphosphonate (DMMP, molecular weight: 124), which is a typical material for a toxic organophosphorus compound, there exist agricultural chemicals containing phosphoric acid such as dichlorvos having a similar chemical structure and organophosphorus pesticides, which are used often, such as malathion, chlorpyrifos, and diazinon. In order to prevent an erroneous detection of these substances, discrimination by using the change tendencies of the detection signals as illustrated in FIG. 10 to FIG. 12 is effective. That is, when the change tendencies of the detection signals detected by each of the detection cells A to D are different depending on the above-stated each substance, application of the discrimination method as stated above enables selective and higher sensitive detection of the detection target substance even when impurities that have a similar molecular weight and a similar constituent element are mixed.

Hereinabove, there is described a method of qualitative detection (the discrimination method) of the molecule to be detected 2 by using the molecular detection apparatus 1 according to the embodiment, but the molecular detection apparatus 1 according to the embodiment can be applied to a quantitative detection of the molecule to be detected 2 without being limited to the qualitative detection of the molecule to be detected 2. That is, the molecular detection apparatus 1 according to the embodiment includes the concentration adjusting unit 20, and the plurality of detection target gases 3 having different concentrations of the molecule to be detected 2 can be generated by the concentration adjusting unit 20. The plurality of detection target gases 3 having different concentrations of the molecule to be detected 2 are sequentially sent to the detection unit 30, and thereby, it is possible to obtain the correlation between the concentration (gas concentration) of the molecule to be detected 2 and the detection signal intensity such as the drain current value as illustrated in each of FIG. 10 to FIG. 12.

As stated above, the correlations between the concentration of the molecule to be detected 2 and the detection signal intensity from the plurality of detection cells A to D are obtained beforehand to discriminate the molecule to be detected 2. A correlation graph between the concentration of the molecule to be detected 2 and the detection signal intensity is used as a calibration curve, and thereby, it is possible to determine the quantity of the concentration of the molecule to be detected 2 in the detection target gas 3 being the detection target from the detection signal intensity (for example, the drain current value) of the detection target gas 3 where the concentration of the molecule to be detected 2 is not diluted or concentrated which is measured by a certain detection cell (any of A to D). The detection cell used to determine the quantity of the concentration of the molecule to be detected 2 is not particularly limited, but it is preferable to use the detection cell where an intensity rate of change (the rate of increase of the rate of decrease) of the detection signal with respect to the concentration change of the molecule to be detected 2 is large, and the intensity change of the detection signal is linearly. It is thereby possible to more accurately determine the quantity of the concentration of the molecule to be detected 2. Besides, it is also possible that two or more detection cells are used, and an average value of the concentrations of the molecule to be detected 2 based on the intensity of these detection signals is set to be a quantified value.

According to the molecular detection apparatus 1 of the embodiment, the discrimination method based on the change tendency of the detection signal according to the concentration change is applied, and thereby, it is possible to selectively and highly sensitively detect the gas molecule having an extremely low concentration in the order of ppt to ppb. Besides, the change tendencies of the detection signals among the plurality of detection cells 301 are analyzed, and thereby, it is possible to improve the discrimination accuracy of the gas molecule. Further, the detection signal intensity based on the concentration change is quantified beforehand, and thereby, it is also possible to determine the quantity of the concentration of the molecule to be detected 2 in the detection target gas 3. Accordingly, it is possible to further enhance detection sensitivity and detection reliability of the gas molecule having an extremely low concentration. Further, the detection sensitivity and the detection accuracy at the detection unit 30 are enhanced, and thereby, the molecular detection apparatus 1 can be further reduced in size. Accordingly, it is possible to provide the molecular detection apparatus 1 where the portability and the detection accuracy are both enabled. The molecular detection apparatus 1 as stated above effectively exerts the functions thereof at various sites such as a disaster site, a site at which an act of terrorism occurs.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The inventions described in the accompanying claims and their equivalents are intended to cover such forms or modifications as would fall within the scope and spirit of the inventions.

What is claimed is:

1. A molecular detection apparatus, comprising:
a concentration adjusting unit configured to dilute and/or concentrate a molecule to be detected in a part of a detection target gas, and generate the detection target gas containing the diluted and/or concentrated molecule to be detected;
a detection unit including a first detection cell and a second detection cell to which a first gas including another part of the detection target gas containing a concentration of the molecule not changed by the concentration adjusting unit and a second gas including the part of the detection target gas containing the diluted and/or concentrated molecule to be detected generated at the concentration adjusting unit are sequentially introduced, the first detection cell configured to output first detection signals based on the concentrations of the molecule to be detected in the first and second gases, and the second detection cell configured to output second detection signals based on the concentrations of the molecule to be detected in the first and second gases;
a first gas flow path to send directly the first gas including the another part of the detection target gas to the detection unit without being passed through the concentration adjusting unit;
a second gas flow path to send the second gas including the part of the detection target gas to the detection unit through the concentration adjusting unit, and
a discrimination unit configured to analyze a first change tendency of the first detection signals and a second change tendency of the second detection signals, and to discriminate the molecule to be detected by the first and second change tendencies,
wherein the first change tendency indicates a first relationship between a change of the concentrations of the molecule to be detected in the first and second gases and a change of intensities of the first detection signals by the first detection cell, and
the second change tendency indicates a second relationship between a change of the concentrations of the molecule to be detected in the first and second gases and a change of intensities of the second detection signals by the second detection cell.

2. The apparatus according to claim 1, wherein each of the first and second detection cells includes a sensor unit, and an organic probe which is provided at the sensor unit and captures the molecule to be detected.

3. The apparatus according to claim 2,
wherein the sensor unit includes a field effect transistor having a graphene layer and a source electrode and a drain electrode connected to the graphene layer, and
wherein the organic probe is provided on the graphene layer.

4. The apparatus according to claim 1,
wherein the concentration adjusting unit includes an adsorber to which the detection target gas containing the molecule to be detected is introduced, and that is configured to adsorb and desorb the molecule to be detected, and wherein the diluted detection target gas is generated by adsorbing the molecule to be detected by the adsorber, or the concentrated detection target gas is generated by desorbing the molecule to be detected adsorbed by the adsorber.

5. The apparatus according to claim 1, wherein the concentration adjusting unit includes:

an adsorber to which a part of the detection target gases containing the molecule to be detected is introduced and that is configured to adsorb the molecule to be detected; and a mixing part configured to mix the detection target gas in which the molecule to be detected is adsorbed by the adsorber with another part of the detection target gases to generate the detection target gas in which the molecule to be detected is diluted.

6. The apparatus according to claim 1,
wherein the concentration adjusting unit includes:

an adsorber to which a part of the detection target gases containing the molecule to be detected is introduced and that is configured to adsorb and desorb the molecule to be detected; and a heater configured to heat the adsorber adsorbing the molecule to be detected to desorb the molecule to be detected, and generate the detection target gas in which the molecule to be detected is concentrated by mixing the desorbed molecule to be detected with another part of the detection target gases.

7. The apparatus according to claim 1, wherein
the concentration adjusting unit is configured to dilute and concentrate the molecule to be detected in the detection target gas, and to generate the plurality of the detection target gases having different concentrations of the molecule to be detected, and the plurality of the detection target gases contain a collected detection target gas which is not diluted and concentrated.

8. The apparatus according to claim 1, wherein
the discrimination unit is configured to further analyze a first change rate of the first detection signals and a second change rate of the second detection signals, and to discriminate the molecule to be detected by the first and second change tendencies and the first and second change rates.

9. A molecular detection method, comprising:
a step collecting a detection target gas containing molecule to be detected;
a first detecting step sending a part of the collected detection target gas to a detection unit including a first detection cell and a second detection cell, and outputting first detection signals based on a concentration of the molecule to be detected in the detection target gas from the first and second detection cells, wherein each of the first detection signals indicates the concentration of the molecule to be detected in the detection target gas without being diluted and concentrated;
a second detecting step diluting and/or concentrating the molecule to be detected in another part of the collected detection target gas, sending the detection target gas in which the molecule to be detected is diluted and/or concentrated to the detection unit including the first and second detection cells after the first detecting step is conducted, and outputting second detection signals based on a concentration of the molecule to be detected in the diluted and/or concentrated detection target gas from the first and second detection cells, wherein each of the second detection signals indicates the concentration of the molecule to be detected in the diluted and/or concentrated detection target gas; and a step analyzing a first change tendency of the first and second detection signals based on the concentrations of the molecule to be detected in the first detection cell and a second change tendency of the first and second detection signals based on the concentrations of the molecule to be detected in the second detection cell, and discriminating the molecule to be detected by the first and second change tendencies of the first and second detection signals in the first and second detection cells, wherein the first change tendency indicates a first relationship between a change of the concentrations of the molecule to be detected in the detection target gas without being diluted and/or concentrated and the diluted and/or concentrated detection target gas and a change of intensities of the first detection signal of the first detection cell in the first detecting step and the second detection signal of the first detection cell in the second detecting step, and the second change tendency indicates a second relationship between a change of the concentrations of the molecule to be detected in the detection target gas without being diluted and/or concentrated and the diluted and/or concentrated detection target gas and a change of intensities of the first detection signal of the second detection cell in the first detecting step and the second detection signal of the second detection cell in the second detecting step.

10. The method according to claim 9, wherein
in the first detecting step, the molecule to be detected is captured by a first organic probe provided at a first sensor unit of the first detection cell and a second organic probe provided at a second sensor unit of the second detection cell, and electrical changes generated at the first and second sensor units when the first and second organic probes capture the molecule to be detected are output as the first detection signals, and
in the second detecting step, the molecule to be detected is captured by the first organic probe provided at the first sensor unit and the second organic probe provided at the second sensor unit, and electrical changes generated at the first and second sensor units when the first and second organic probes capture the molecule to be detected are output as the second detection signals.

11. The method according to claim 9, wherein the second detecting step includes:
a step adsorbing the molecule to be detected in the detection target gas by an adsorber; and
a step outputting the second detection signals depending on the detection target gas which is diluted by adsorbing the molecule to be detected by the adsorber, or outputting the second detection signals depending on the detection target gas which is concentrated by desorbing the molecule to be detected which are adsorbed by the adsorber.

12. The method according to claim 9, wherein the second detecting step includes:
a step introducing a part of the detection target gas to an adsorber and adsorbing the molecule to be detected by the adsorber; and
a step generating the detection target gas in which the molecule to be detected is diluted by mixing the detection target gas in which the molecule to be detected are adsorbed by the adsorber with another part of the detection target gas, and outputting the second detection signals depending on the diluted detection target gas.

13. The method according to claim 9, wherein the second detecting step includes:
   a step introducing a part of the detection target gas to an adsorber capable of adsorbing and desorbing the molecule to be detected and adsorbing the molecule to be detected by the adsorber; and
   a step generating the detection target gas in which the molecule to be detected is concentrated by desorbing the molecule to be detected by heating the adsorber which adsorbs the molecule to be detected to mix the desorbed molecule to be detected with another part of the detection target gas, and outputting the second detection signals depending on the concentrated detection target gas.

14. The method according to claim 9, wherein
   the second detecting step comprises: a first step which includes diluting the molecule to be detected in the collected detection target gas, sending the detection target gas in which the molecule to be detected is diluted to the detection unit including the first and second detection cells, and outputting third detection signals based on a concentration of the molecule to be detected in the diluted detection target gas from the first and second detection cells; and a second step which includes concentrating the molecule to be detected in the collected detection target gas, sending the detection target gas in which the molecule to be detected is concentrated to the detection unit including the first and second detection cells, and outputting fourth detection signals based on a concentration of the molecule to be detected in the concentrated detection target gas from the first and second detection cells, and
   the analyzing and discriminating step is that a first change tendency of the first, third and fourth detection signals based on the concentrations of the molecule to be detected in the first detection cell, and a second change tendency of the first, third and fourth detection signals based on the concentrations of the molecule to be detected in the second detection cell, and the molecule to be detected is discriminated by the first and second change tendencies of the first, third and fourth detection signals in the first and second detection cells.

\* \* \* \* \*